United States Patent [19]

Hui et al.

[11] Patent Number: 6,001,810
[45] Date of Patent: Dec. 14, 1999

[54] METHODS FOR TREATING RETROVIRAL INFECTION

[75] Inventors: Kwan Yuk Hui; Mei-Huei T. Lai, both of Carmel, Ind.

[73] Assignee: Eli Lilly and Company, Indianapolis, Ind.

[21] Appl. No.: 07/576,538

[22] Filed: Aug. 31, 1990

Related U.S. Application Data

[63] Continuation-in-part of application No. 07/439,204, Nov. 20, 1989, abandoned.

[51] Int. Cl.$^6$ .............................. A61K 38/08; C07K 7/06
[52] U.S. Cl. ................................ 514/17; 514/16; 514/15; 530/327; 530/328; 530/329; 530/330
[58] Field of Search ................ 514/15–17; 530/327–330

[56] References Cited

U.S. PATENT DOCUMENTS

| | | | |
|---|---|---|---|
| 4,880,779 | 11/1989 | Gallaher | 514/17 |
| 4,925,748 | 5/1990 | Ikoma et al. | 435/5 |
| 4,952,493 | 8/1990 | Kettner et al. | 435/5 |
| 4,956,273 | 9/1990 | Kennedy et al. | 435/5 |
| 5,001,049 | 3/1991 | Klein et al. | 435/5 |
| 5,055,391 | 10/1991 | Montagnier et al. | 435/5 |

OTHER PUBLICATIONS

Von der Helm, et. al., 1989, *FEBS Letters* 247(2):349–352.
Lai et al., 1989, Slides from a presentation made at the 1989 RNA Tumor Viruses Meeting in Cold Spring Harbor, New York, May 24–28, 1989.
Seelmeier et al., 1988, *Proc. Natl. Acad. Sci. USA*, 85:6612–6616.
Graves et al., 1988, *Proc. Natl. Acad. Sci. USA*, 85:2449–2453.
DeBouck et al., 1987, *Proc. Natl. Acad. Sci. USA*, 84:8903–8906.
Mous et al., 1988, *J. Virol.*, 62:1433–1436.
Hansen et al., 1988, *EMBO J.*, 7:1785–1791.
Lillihoj et al., 1988, *J. Virol.*, 62:3053–3058.
Richards et al., 1989, *FEBS Letters*, 247:113–117.
Moore et al., 1989, *Biochem. Biophys. Res. Comm.*
Billich et al., 1988, *J. Biol. Chem.*, 263:17905–17908.
Bu et al., 1989, *AIDS Res. and Human Retroviruses*, 5:259–268.
Blumenstein et al., 1989, *Biochem. Biophys. Res. Comm.*, 163:980–987.
Marchetto et al., 1989, Abstract from 5th International Conference on AIDS, Jun. 4–9 (Montreal, Canada) abstract No. Th.C.P.66.
Meek et al., 1989, is a hand–out distributed at the Jul., 1989, Gordon Conference on Medicinal Chemistry.
Sawyer et al., 1989, is an abstract (P–33) from the Eleventh American Peptide Symposium held on Jul. 9–14 at La Jolla, CA.
Hui et al., 1989, is an abstract (#P–103) presented at the Eleventh American Peptide Symposium held Jul. 9–14 La Jolla, CA.
Hui et al., 1987, *J. Med. Chem.*, 30:1287–1295.
Hui et al., 1988, *J. Med. Chem.*, 31:1679–1686.
Tomasseli et al., 1990, *Biochemistry*, 29:264–269.
Meek et al., 1989, *Proc. Natl. Acad. Sci. USA*, 86:1841–1845.
Dreyer et al., 1989, *Proc. Natl. Acad. Sci. USA*, 86:9752–9756.
Meek et al., 1990, *Nature*, 343:90–92.
Roberts et al., 1990, *Science*, 248:358–361.

*Primary Examiner*—Ponnathapura Achutamurthy
*Assistant Examiner*—T. D. Wessendorf
*Attorney, Agent, or Firm*—Arlene K. Musser; Janet T. McClain

[57] ABSTRACT

The present invention provides antiretroviral methods using the compounds of formula (I)

$$X\text{-}X1\text{-}P1\text{-}Val\text{-}Z\text{-}Leu\text{-}P2\text{-}Y$$

wherein:

Z is Statine or ACHPA;
and when Z is Statine,
  X is H-Pro-paF, H-Pro-His, Ac-Tyr, Ac-NA, Ac-Trp, Ac-YOM, Ac-Phe, Ac-paF, H-His, Ac-His or Ac-Gly-Tyr-YOM,
  X1 is Pro Ser or Ac,
  P1 is Phe, paF or YOM,
  P2 is Phe or Leu, and
  Y is $NH_2$, paF—$NH_2$, His—$NH_2$, Phe—$NH_2$ or Tyr-Lue—$NH_2$,
provided that when X1 is Ac then there is no X residue;
and when Z is ACHPA,
  X is H-Pro-His, H-Pro-paF, Ac-paF or Ac-His,
  P1 is Phe,
  P2 is Phe, and
  Y is paF—$NH_2$ and His—$NH_2$.

The invention further provides methods for determining the retroviral protease inhibitory activity of compounds using viral polypeptides made using recombinant DNA techniques.

48 Claims, 4 Drawing Sheets

Restriction Site and Function Map of Plasmid pHP10D pHP10D

Restriction Site and Function Map of Plasmid pHGAG pHGAG

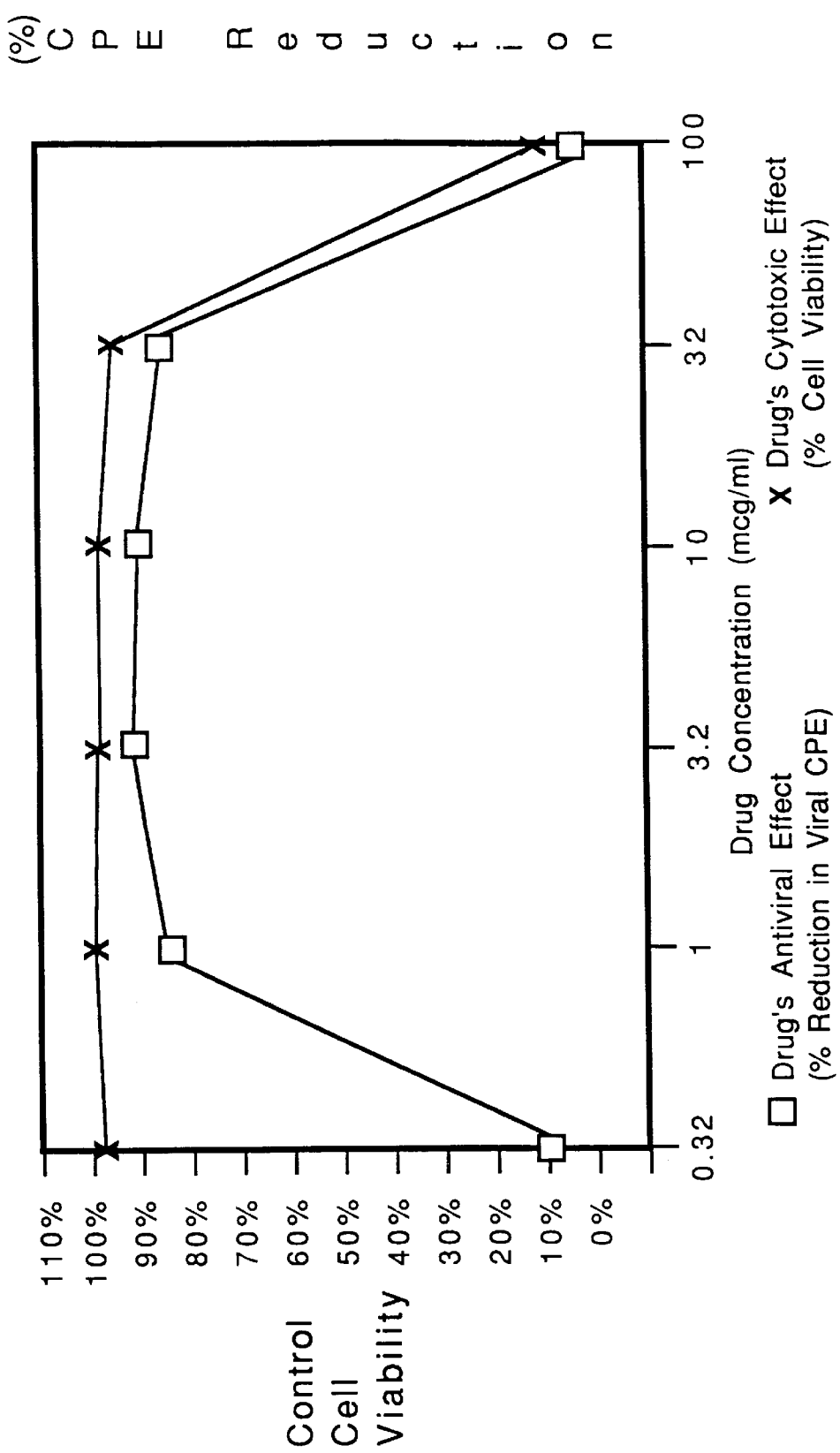

METHODS FOR TREATING RETROVIRAL INFECTION

CROSS REFERENCE

This application is a continuation-in-part of U.S. patent application Ser. No. 07/439,204, filed Nov. 20, 1989, abandoned.

BACKGROUND OF THE INVENTION

Diseases caused by retroviruses are becoming alarmingly prevalent. Sexually transmitted retroviral infections and those transmitted by blood transfusion have been the focus of intensive research efforts over the past several years. The tools of modern molecular biology have yielded many of the secrets of retroviral infection, maturation and replication. The present invention concerns the discovery that certain short peptides are useful in treating retroviral infections because the peptides can inhibit the action of the retroviral proteases. The invention also relates to methods for discovering other compounds which display retroviral protease inhibitory activity.

SUMMARY OF THE INVENTION

Acquired immune deficiency syndrome (AIDS) has been one of the major health-care concerns of the past several years. The causative agent of the disease is a human retrovirus referred to as Human Immuno-deficiency Virus type-1 (HIV-1). The HIV-1 genome encodes structural protein precursors known as gag and pol, which are processed to yield the retroviral protease (PR), reverse transcriptase (RT) and endonuclease/integrase (IN). The protease further cleaves the gag protein to yield mature HIV-1 proteins known as p6, p7, p17 and p24. The present invention provides methods for the discovery of HIV-1 protease inhibitors based upon the high level expression of the HIV-1 gag and pol genes in *Escherichia coli*.

Also disclosed and claimed is a method of inhibiting HIV-1 protease activity and thereby treating an HIV-1 infection by administering an antiviral amount of a compound or compounds which are short peptides. These peptides effectively inhibit the activity of the HIV-1 protease and thereby prevent the maturation and replication of the virus.

For purposes of the present invention, as disclosed and claimed herein, the following terms and abbreviations are as defined below.

Ac—An acetyl group.
ACHPA—a (3S,4S)-4-amino-3-hydroxy-5-cyclohexylpentanoic acid residue.
AHPPA—a (3S,4S)-4-amino-3-hydroxy-5-phenylpentanoic acid residue.
AVA—an aminovaleric acid residue.
Ala—an alanine residue.
$Ap^R$—the ampicillin-resistant phenotype or gene conferring same.
Arg—an arginine residue.
Asn—an asparagine residue.
Asp—an aspartic acid residue.
Boc—tert-butyloxycarbonyl.
Cys—a cysteine residue.
Fmoc amino acids—amino acids with 9-Fluorenylmethoxycarbonyl as a protecting group.
Gln—a glutamine residue.
Glu—a glutamic acid residue.
Gly—a glycine residue.
H—hydrogen.
His—a histidine residue.
Ile—an isoleucine residue.
Lys—a lysine residue.
Met—a methionine residue.
NA—a naphthylalanine residue, in particular 3-(1'-naphthyl)alanine.
$NH_2$—an amide group.
paF—a para-aminophenylalanine residue.
Phe—a phenylalanine residue.
$P_L$—a DNA segment comprising the promoter activity of the bacteriophage λ leftward promoter.
Pro—a proline residue.
Promoter—a DNA sequence that directs transcription of DNA into RNA.
Recombinant DNA Cloning Vector—any autonomously replicating agent, including, but not limited to, plasmids and phages, comprising a DNA molecule to which one or more additional DNA segments can be or have been added.
Recombinant DNA Expression Vector—any recombinant DNA cloning vector into which a promoter has been incorporated.
Restriction Fragment—any linear DNA sequence generated by the action of one or more restriction endonuclease enzymes.
R,S-Sta—a (3R,4S)-4-amino-3-hydroxy-6-methylheptanoic acid residue.
Sensitive Host Cell—a host cell that cannot grow in the presence of a given antibiotic or other toxic compound without a DNA segment that confers resistance thereto.
Ser—a serine residue.
Statine—a (3S,4S)-4-amino-3-hydroxy-6-methylheptanoic acid residue.
Structural Gene—any DNA sequence that encodes a functional polypeptide, inclusive of translational start and stop signals.
$Tc^R$—the tetracycline-resistant phenotype or gene conferring same.
Thr—a threonine residue.
Trp—a tryptophan residue.
Tyr—a tyrosine residue.
Val—a valine residue.
YOM—an O-methyltyrosine residue.

BRIEF DESCRIPTION OF THE FIGURES

FIG. 4—a chart displaying the cytopathic effect and antiviral effect of peptide P-7. In the figure, a block represents the peptide's antiviral effect at a given concentration while an X represents the peptide's cytotoxic effect at a given concentration.

DETAILED DESCRIPTION OF THE INVENTION

Figure 1:
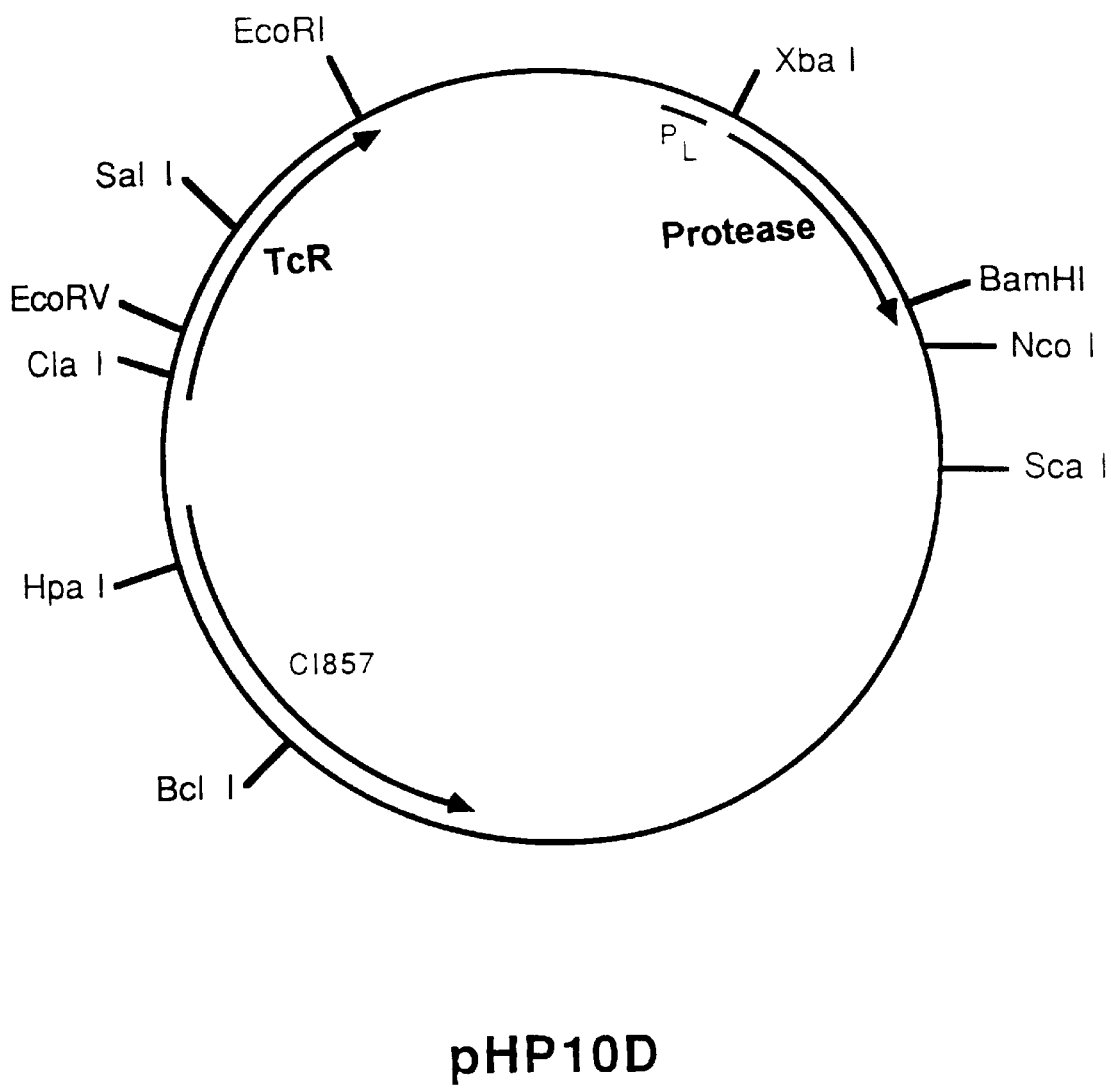
FIG. 1—the restriction site and function map of plasmid pHP10D. For purposes of the present disclosure, plasmid maps are not drawn exactly to scale.

The present invention comprises methods for preventing, treating and controlling retroviral infections. More particularly one embodiment provides an antiviral method which comprises administering an antiviral amount of a compound of the formula (I):

X-X1-P1-Val-Z-Leu-P2-Y wherein:

Z is Statine or ACHPA;
and when Z is Statine,

X is H-Pro-paF, H-Pro-His, Ac-Tyr, Ac-NA, Ac-Trp, Ac-YOM, Ac-Phe, Ac-paF, H-His, Ac-His, or Ac-Gly-Tyr-YOM,

X1 is Pro, Ser or Ac,

P1 is Phe, paF or YOM,

P2 is Phe or Leu, and

Y is $NH_2$, paF—$NH_2$, His—$NH_2$, Phe—$NH_2$ or Tyr-Lue—$NH_2$, provided that when X1 is Ac then there is no X residue;
and when Z is ACHPA, X is H-Pro-His, H-Pro-paF, Ac-PaF or Ac-His, P1 is Phe, P2 is Phe, and Y is paF—$NH_2$ and His—$NH_2$.

In addition to the substitutions listed above, X, X1, P1, P2 and Y could be selected from any of the naturally or non-naturally occurring amino acids, either in protected or unprotected form. Z could also be 4-amino-3-hydroxy-5-phenylpentanoic acid (AHPPA) or aminovaleric acid (AVA), as well as the Statine or ACHPA residues and their analogues or structural variants mentioned above.

Another embodiment of the present invention is an antiviral method comprising the administration of an antiviral amount of a compound of the formula (II):

X-Pro-Phe-Val-Statine-Leu-P2-Y, wherein:

X is H-Pro-paF, H-Pro-His, Ac-Tyr, Ac-NA, Ac-Trp, Ac-YOM, Ac-Phe, Ac-paF, H-His, Ac-His or Ac-Gly-Tyr-YOM,

P2 is Phe or Leu and

Y is $NH_2$, paF—$NH_2$, His—$NH_2$ Phe—$NH_2$ or Tyr-Lue—$NH_2$.

Furthermore, X, P2 and Y may be selected from any of the naturally or non-naturally occurring amino acids, either in protected or unprotected form. X and Y can be represented by short peptides rather than single amino acids, as long as the peptide retains its ability to inhibit the activity of retroviral protease. Skilled artisans will readily recognize that the pentapeptide core of this retroviral protease inhibitor is an important element of the present invention.

A preferred embodiment of the present invention is an antiviral method comprising the administration of an antiviral amount of a compound of the formula (III):

X-Pro-Phe-Val-Statine-Leu-Phe—$NH_2$, wherein:

X is Ac-Tyr, Ac-NA, Ac-Trp, Ac-YOM, Ac-Phe or Ac-Gly-Tyr-YOM.

The substitutions listed above for X could also be selected from any of the naturally or non-naturally occurring amino acids, either in protected or unprotected form. A particularly preferred embodiment is that wherein the compound has the formula Ac-NA-Pro-Phe-Val-Statine-Leu-Phe—$NH_2$. Another particularly preferred embodiment is that wherein the compound has the formula Ac-YOM-Pro-Phe-Val-Statine-Leu-Phe—$NH_2$. Yet another particularly preferred embodiment is that wherein the compound has the formula Ac-Gly-Tyr-YOM-Pro-Phe-Val-Statine-Leu-Phe—$NH_2$. Various protease inhibitors of the present invention are shown in Table 1.

TABLE I

| | | | | |
|---|---|---|---|---|
| P-1 | H-Pro paF Pro Phe Val | Statine | Leu Phe paF $NH_2$ |
| P-2 | H-Pro His Pro Phe Val | ACHPA | Leu Phe paF $NH_2$ |
| P-3 | H-Pro paF Pro Phe Val | ACHPA | Leu Phe paF $NH_2$ |
| P-4 | Ac paF Pro Phe Val | ACHPA | Leu Phe paF $NH_2$ |
| P-5 | Ac Tyr Pro Phe Val | Statine | Leu Phe $NH_2$ |
| P-6 | Ac His Pro Phe Val | Statine | Leu His $NH_2$ |
| P-7 | Ac NA Pro Phe Val | Statine | Leu Phe $NH_2$ |
| P-8 | Ac Trp Pro Phe Val | Statine | Leu Phe $NH_2$ |
| P-9 | Ac YOM Pro Phe Val | Statine | Leu Phe $NH_2$ |
| P-10 | Ac Phe Pro Phe Val | Statine | Leu Phe $NH_2$ |
| P-11 | H-Pro His Pro Phe His | Statine | Leu Phe $NH_2$ |
| P-12 | Ac paF Pro paF Val | Statine | Leu Phe paF $NH_2$ |
| P-13 | Ac paF Pro YOM Val | Statine | Leu Phe paF $NH_2$ |
| P-14 | Ac paF Pro Phe Val | Statine | Leu Phe paF $NH_2$ |
| P-15 | H-His Pro Phe Val | Statine | Leu Phe paF $NH_2$ |
| P-16 | Ac His Pro Phe Val | ACHPA | Leu Phe His $NH_2$ |
| P-17 | Ac His Pro Phe Val | ACHPA | Leu Phe paF $NH_2$ |
| P-18 | Ac His Pro Phe His | ACHPA | Ile Phe $NH_2$ |
| P-19 | H-Pro His Pro Phe His | Statine | Ile His $NH_2$ |
| P-20 | Ac His Pro Phe Val | Statine | Leu Phe Leu $NH_2$ |
| P-21 | Ac His Pro Phe Val | Statine | Leu Phe Phe $NH_2$ |
| P-22 | Ac His Pro Phe Val | Statine | Leu Leu Phe $NH_2$ |
| P-23 | H-Pro His Pro Phe His | Statine | Ile Phe $NH_2$ |
| P-24 | H-Pro His Pro Phe His | AHPPA | Ile Phe $NH_2$ |
| P-25 | H-Pro His Pro Phe His | AVA | Ile Phe $NH_2$ |
| P-26 | Ac paF Pro Phe Val | Statine | Leu Phe $NH_2$ |
| P-27 | Ac NA Ser Phe Val | Statine | Leu Phe $NH_{22}$ |
| P-28 | H-Pro paF Pro Phe Val | R, S-Sta | Leu Phe paF $NH_2$ |
| P-29 | Ac Gly Tyr YOM Pro Phe Val | Statine | Leu Phe $NH_2$ |
| P-30 | Ac YOM Pro Phe Val | Statine | Leu Phe Tyr Leu $NH_2$ |
| P-31 | Ac Phe Val | Statine | Leu Phe $NH_2$ |

The skilled artisan will recognize that a key component of the present invention is the tetrapeptide core found between the Proline and P2 residues within the compound of formula (II):

X-Pro-Phe-Val-Statine-Leu-P2-Y.

Using peptide P-9 as a standard, it can be demonstrated that extending the amino terminus at the X position can increase the potency of protease inhibitor. The P-29 peptide (Ac-Gly-Tyr-YOM-Pro-Phe-Val-Statine-Leu-Phe—$NH_2$) is three times more potent than the P-9 peptide (Ac-YOM-Pro-Phe-Val-Statine-Leu-Phe—$NH_2$). Extending the carboxy terminus at the Y position can also increase the potency of the protease inhibitor. The P-30) peptide (Ac-YOM-Pro-Phe-Val-Statine-Leu-Phe-Tyr-Leu—$NH_2$) is about 1.5 times more active than the P-9 peptide (Ac-YOM-Pro-Phe-Val-Statine-Leu-Phe—$NH_2$). A peptide in which the position of the residue X is shifted by the removal of the Proline residue from P-30 (Ac-YOM-Phe-Val-Statine-Leu-Phe-Tyr-Lue—$NH_2$) was totally inactive. However, an assay comparing P-7 to P-27 demonstrates that the proline residue can be substituted by a serine residue without significantly affecting the potency of P-27.

The potency of the inhibitory peptides may also be affected by altering the residue(s) at the X position. For example, replacing the naphthylalanyl residue at position X in P-7 with an O-methyltyrosyl (P-9) or a para-aminophenylalanyl (P-26) residue increases the potency three to four times. Deleting the amino terminal dipeptide NA-Pro (P-7) or YOM-Pro (P-9) results in a pentapeptide analogue (P-31) which is as potent as the P-7 and P-9 peptides, whereas further shortening of the sequence by deleting the amino terminal Phe created the peptide Ac-Val-Statine-Leu-Phe—$NH_2$ which was inactive.

Replacement of the Valine residue found in peptides P-7, P-9 and P-31 with Histidine residues created peptides which demonstrated no inhibitory activity against the HIV protease. Optical chivality of the statine residue is not mandatory for activity. However, (S,S) Statine (i.e., P-1) yields an inhibitor which is 20 times more potent than the R,S-diastereomer (P-28). The skilled artisan can therefore readily discern that the tetrapeptide found in the core of the peptide of formula (II) is an important characteristic of the present invention. Indeed, it may also be noted that the Val-Statine-Leu tripeptide is quite important to the present invention.

The retrovirus protease inhibitors used in this invention can be prepared by any of a variety of recognized peptide synthesis techniques including classical (solution) methods, solid-phase methods, semisynthetic methods and the more recently available recombinant DNA methods.

In the solid-phase technique, the amino acid sequence is constructed sequentially from an initial, insoluble, resin-supported C-terminal amino acid. Techniques for the solid phase method are described by J. Stewart et al., *Solid-Phase Peptide Synthesis, 2d Edition*, Pierce Chemical Co., Rockford, Ill., 1984, the entire teaching of which is herein incorporated by reference.

In general, in the solid-phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequential until the desired amino acid sequence is obtained. Alternatively, small peptide fragments can be prepared and introduced into the peptide chain in the desired order. The peptide chain remains attached to the resin throughout synthesis, and, upon completion of the chain, the peptide is cleaved from the resin.

The peptide chain is attached to the polystyrene resin by means of a covalent linkage formed between the carboxyl group of the C-terminal moiety and a specific functional group present on the resin matrix as a site for such attachment.

The amino acids are coupled using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, or isobutyl chloroformate. Alternatively, the amino acid can be converted to an active ester such as a 2,4,5-trichlorophenyl ester, a pentachlorophenyl ester, a pentafluorophenyl ester, a p-nitrophenyl ester, a N-tert-Butoxycarbonyl ester, a N-hydroxysuccinimide ester, or an ester formed from 1-hydroxybenzotriazole.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. See Schroder and Lubke, *The Peptides*, Academic Press, 1965, Chapter III and U.S. Pat. No. 4,259,234 are which incorporated herein by reference.

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g., sulfhydryl, ε-amino, β-and γ-carboxyl, imidazole, guanido and hydroxyl), and that such functional groups must also be protected, both during the initial and subsequent coupling steps. Suitable protecting groups are known in the art. See for example, *Protective Groups In Organic Chemistry*, M. McOmie, Editor, Plenum Press, N.Y., 1973 and. U.S. Pat. No. 4,617,149 which is incorporated herein by reference.

In selecting a particular protecting group, certain conditions must be observed. An α-amino protecting group (1) must render the α-amino function inert under the conditions employed in the coupling reaction, (2) must be readily removable after the coupling reaction under conditions that will not remove side chain protecting groups and will not alter the structure of the peptide fragment, and (3) must eliminate the possibility of racemization upon activation immediately prior to coupling. A side chain protecting group (1) must render the side chain functional group inert under the conditions employed in the coupling reaction, (2) must be stable under the conditions employed in removing the α-amino protecting group, and (3) must be readily removable, if necessary, upon completion of the desired amino acid sequence under reaction conditions that will not alter the structure of the peptide chain.

It will be apparent to those skilled in the art that the protecting groups known to be useful for peptide synthesis will vary in reactivity to the agents employed for their removal. For example, certain protecting groups, such as triphenyl methyl and 2-(p-biphenylyl) isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl, are less labile and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, isopropyloxycarbonyl, and 9-fluorenylmethoxycarbonyl (Fmoc), are even less labile and require stronger acids, such as hydrogen fluoride, hydrogen bromide, or boron trifluoroacetate in trifluoroacetic acid, for their removal.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid anhydrous hydrogen fluoride. This reagent not only will cleave the peptide from the resin but may also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid hydrogen fluoride. A particularly useful technique for the creation of peptides like those of this invention is described in Hui, K. Y. et al., 1988, J. Med. Chem. 31:1679–1686, the teaching of which is herein incorporated by reference.

Another method for cleaving the protected peptide from the resin is by ammonolysis or by treatment with hydrazine. If desired, the resulting C-terminal amide or hydrazide can be hydrolyzed to the free C-terminal carboxyl, and the protecting groups can be removed conventionally.

It will also be recognized that the protecting group present on the N-terminal α-amino group may be removed preferentially either before, after or simultaneously with the cleavage of the protected peptide from the resin support.

The peptides used in the present invention may also be constructed using automated synthesizers, such as the Applied Biosystems 430A peptide synthesizer. Both naturally and non-naturally occurring amino acids are commercially available, in both the protected and unprotected form, from a wide variety of commercial sources. The techniques and sources for starting materials set forth in the Examples are provided as a means of illustrating the invention and are not to be construed as a limitation thereon.

Each of the peptides listed in Table 1, infra, was tested for its ability to inhibit the activity of the HIV-1 protease using the in vitro screening method of the present invention. The three major structural genes of HIV-1 are arranged in the viral genome in the order of 5'-gag-pol-env-3'. The gag gene encodes four group-specific antigens known as MA(p17), CA(p24), NC(p7) and p6. The pol gene encodes the viral protease, the reverse transcriptase/ribonuclease H and the viral integrase. The primary translational product of the gag gene is a 55-KDa polyprotein ($pr55^{gag}$), while the primary translation product of the pol gene is a gag-pol fusion protein 160 KDa in size ($pr160^{gag-pol}$) which is achieved by a ribosomal frameshift near the 3' end of the gag gene. The retrovirus protease is an aspartyl protease which is liberated from the $pr160^{gag-pol}$ polypeptide by autocatalysis. The protease then acts upon the gag polypeptide to cleave it into the mature p17, p24, p7 and p6 proteins. Any agent which inhibits the retrovirus protease will therefore effectively prevent the maturation of infectious retrovirus particles.

To perform the protease assay of the present invention, genes encoding the protease and gag precursor were first cloned and expressed in *Escherichia coli* K-12 L507 cells. Plasmid pHP10D, which contains the HIV-1 protease gene, was transformed into *E. coli* K12 L507 to produce the HIV-1 protease. Plasmid pHP10D can be conventionally isolated from *E. coli* K12 L507/pHP10D, deposited (on Nov. 14, 1989) and made part of the permanent stock culture collection of the Northern Regional Research Laboratory (NRRL), Peoria, Ill. A culture of *E. coli* K12 L507/pHP10D can be obtained from the NRRL under the accession number NRRL B-18560. Plasmid pHP10D comprises a gene encoding the first 56 amino acids of the pol open-reading frame (ORF), a gene encoding the mature HIV-1 protease of 99 amino acids and a gene encoding the first 144 amino acids of the HIV-1 reverse transcriptase fused to the last 58 codons of the bovine growth hormone gene. Expression of these genes on plasmid pHP10D is driven by the bacteriophage lambda $P_L$ promoter, which functions most efficiently when the thermal-labile $CI^{857}$ repressor is not active in the host cell. A restriction site and function map of plasmid pHP10D is presented in FIG. 1 of the accompanying drawings.

Figure 2:
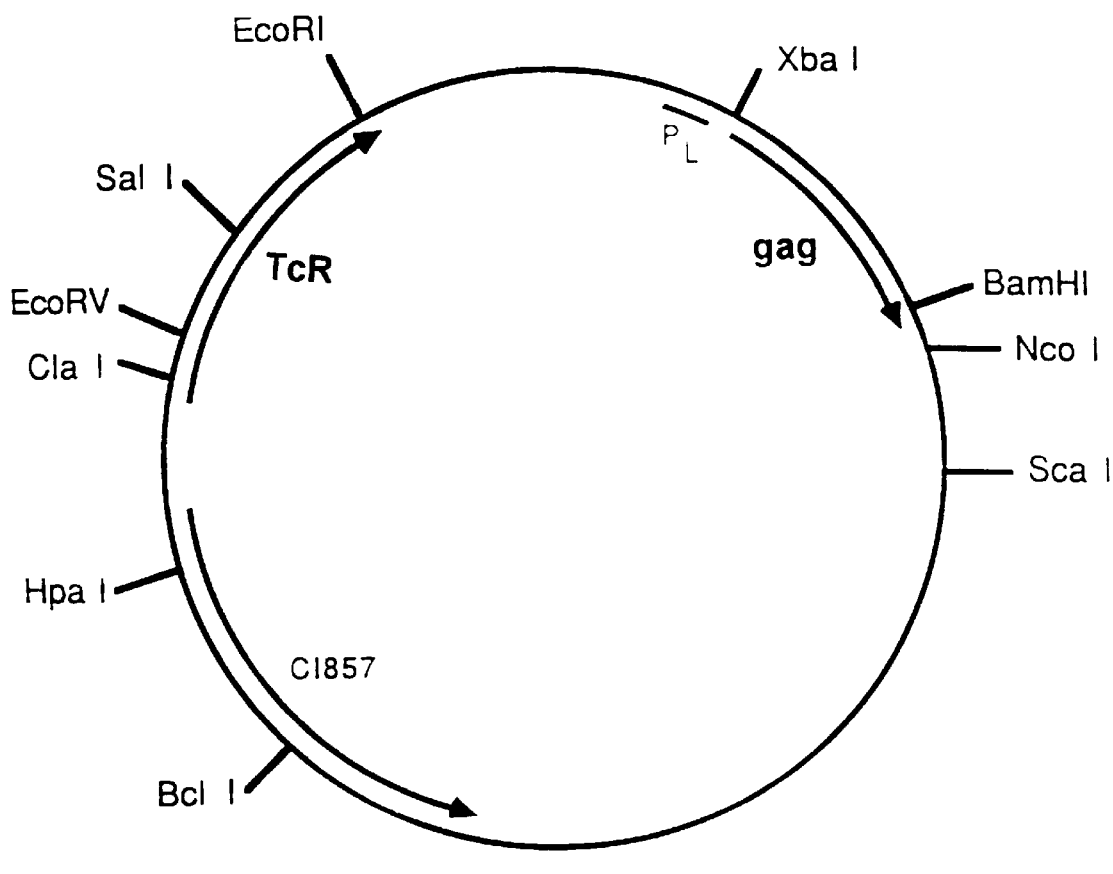
FIG. 2—the restriction site and function map of plasmid pHGAG.

Plasmid pHGAG comprises a gene encoding the HIV-1 gag polypeptide, the expression of which is also driven by the bacteriophage lambda $P_L$ promoter under appropriate conditions in the proper host cell. Plasmid pHGAG can be conventionally isolated from *E. coli* K12 L507/pHGAG, also deposited (on Nov. 14, 1989) and made part of the permanent stock culture collection of the NRRL. A culture of *E. coli* K12 L507/pHGAG can be obtained from the NRRL under the accession number NRRL B-18561. A restriction site and function map of plasmid pHGAG is presented in FIG. 2 of the accompanying drawings.

*E. coli* K12 L507/pHP10D was inoculated into L-Broth containing 12.5 μg/ml of tetracycline, the culture was grown to mid-log phase at 32° C., then the temperature was shifted quickly to 40° C. After 2.5 to 3 hours, the cells were concentrated, chilled, treated with lysozyme and sonicated to release the HIV-1 protease, 80% of which remains bound to the cellular debris of the crude lysate. In an analogous manner, the gag polypeptide was produced by expressing the genes encoded on plasmid pHGAG in *E. coli* K12 L507. For the gag polypeptide, however, the culture was left at 40° C. for about 4 hours. Approximately 10% of the gag polypeptide is found in the supernatant after cell lysis. The gag polyprotein present in the supernatant fraction is used as the substrate for the assay.

A 100 μl control reaction was established containing 10 to 20 μl of crude protease, about 2 μl of the gag supernatant and final concentrations of 50 mM MES Buffer (pH 5.5), 1 mM DTT and 25 mM NaCl. Inhibition assays were performed by pre-incubating the crude protease with an inhibitory compound at room temperature for about 30 minutes before adding the gag supernatant to the reaction. Both the control and the experimental reactions were incubated from three to sixteen hours at 37° C. The reactions were then electrophoresed and blotted onto nitrocellulose filters. Monoclonal antibodies which recognize epitopes on p24 and p17 viral proteins were contacted with the filter then visualized using standard biotinylation or radionuclear techniques. Compounds which prevented the maturation of the gag polypeptide into mature viral proteins p24 and p17 were then ranked according to their HIV-1 protease inhibitory activity.

Skilled artisans will recognize that the expression of HIV-1 genes in bacteria is in no way limited to *Escherichia coli*. Other genera of bacteria, such as Bacillus sp. and Streptomyces sp., are also useful for the production of heterologous proteins. Those skilled in the art will also recognize that when heterologous polypeptides are expressed in *E. coli*, a wide variety of promoters and phenotypic determinant genes are available for use. Many different promoter systems and resistance-conferring genes are known in the art, and can be constructed either synthetically or from known plasmids.

The compounds of formula (I) were found to be effective in the retroviral protease inhibition method of the present invention. The method is useful to prevent the maturation of the gag precursor polypeptide which may be present in a wide variety of biological solutions. For example, an antiviral amount of any of the peptides of formula (I) can be added to a sample of human blood, serum or plasma to inhibit any retroviral protease that may be present in the sample. The gag polypeptide could then be more readily removed as a contaminant from the biological solution.

In addition to the HIV-1 protease inhibitory activity of the compounds of formula (I), the compounds of formulas (II) and (III) are also widely useful in an antiviral method for use in cell culture and in vivo. The peptides were tested for antiviral effect against both HIV-1 and Murine Leukemia Virus (MLV) and significantly increased the survival rates of cells infected with these viruses. Other retroviruses, infections by which can be prevented or treated by the methods of the present invention are the C-type retrovirus which causes lymphosarcoma in Northern Pike, the C-type retrovirus which infects mink, the caprine lentivirus which infects sheep, the Equine Infectious Anemia Virus (EIAV), the C-type retrovirus which infects pigs, the Avian Leukosis Sarcoma Virus (ALSV), the Feline Leukemia Virus (FeLV), the Feline Aids Virus, the Bovine Leukemia Virus (BLV), the Simian Leukemia Virus (SLV), the Simian Immunodeficiency Virus (SIV), the Human T-cell Leukemia Virus type-I (HTLV-I), the Human T-cell Leukemia Virus type-II (HTLV-II), and the Human Immunodeficiency virus type-2 (HIV-2). Those skilled in the art will note that the methods of the present invention would be most useful in treating both HIV-1 and HIV-2 infections, as the amino acid sequence of the HIV-2 protease is 73% homologous to the protease of HIV-1.

Skilled artisans will recognize that the antiviral activity, displayed in cell culture by the compounds used in the present method demonstrates the utility of the compound for use in vivo. The compounds can be administered either parentally (intravenously, intramuscularly or subcutaneously) or by inhalation or the intranasal route to a mammal suffering from a retroviral infection or susceptible thereto. For parenteral administration, as by the intraperitoneal route, the compound may be dissolved or suspended in water containing 2% of a surface active agent, particularly an emulfor (a polyhydroxylated fatty acid). For intravenous administration, the compound can be dissolved in one of the commonly used intravenous fluids such as physiological saline, Ringer's solution or 5% dextrose solution and the like. For intramuscular preparations a sterile formulation of a suitable salt form of the compound (for example, the hydrochloride salt or sodium salt) can be formulated with a "suitable vehicle." Examples of such sterile formulations are a suitable salt form either dissolved in a pharmaceutical diluent (for example, Water-for-Injection, physiological saline, 5% glucose) or suspended in an aqueous base or a pharmaceutically acceptable oil base (for example, an ester of a long chain fatty acid such as ethyl oleate).

To practice the antiviral method of this invention, all that is required is that an antiviral amount of an antiviral agent be added to the tissue culture to be protected, or be administered to an animal suffering from or susceptible to a viral infection. The compounds will ideally be formulated with pharmaceutically acceptable diluents for convenient administration, for example parenterally, and can be employed for prophylatic as well as therapeutic treatment. The formulations will normally contain from about 1 to about 95% by weight of active antiviral agent.

For severe viral infections, the antiviral compounds will be formulated for intravenous or intramuscular administration. Such formulations will contain from about 1 to about 50% active agent. The compounds will be dissolved in common diluents such as isotonic saline of dextrose solutions, for intravenous infusion, and can be dissolved in polyhydric aliphatic alcohols such as propylene glycol or polyethylene glycol for easy intravenous or intramuscular injection.

Pharmaceutically acceptable salts can be prepared from those compounds of the above formula sufficiently acidic or basic to react with common organic and inorganic acids and bases such as hydrochloric acid, succinic acid, sodium hydroxide, and the like. The pharmaceutically acceptable salts generally have enhanced solubility characteristics compared to the compound from which they are derived, and thus are often more amenable to formulation as liquids or emulsions.

The antiviral agents described above are active over a wide range of dose levels. While the particular dose to be administered will be determined by the precise viral infection to be treated or guarded against and its severity, the route of administration, and related circumstances that will be determined by attending medical practitioners, the normal dose will range from about 0.1 to about 100 mg/kg.

In a preferred method of treatment, the compounds are administered to mammals susceptible to infection with retrovirus including horses, mice, pigs, sheep and humans. Among humans, the compounds are administered prophylactically particularly to persons who are at risk of a retroviral infection.

The following Examples are provided as a means of illustrating the present invention and are not to be construed as a limitation thereon.

EXAMPLE 1

Synthesis of N-[(1,1-dimethylethoxy)carbonyl]-4-[[(9H-fluoren-9-ylmethoxy)carbonyl]amino]-L-phenylalanine (Boc-paF(Fmoc))

Boc-para-aminophenylalanine (2.6 mmol; 0.72 g) was dissolved in 12 ml of dichloromethane (DCM) (from Dow Chemical, Midland, Mich.) containing 3.85 mmol of triethylamine (TEA) (from Aldrich, Milwaukee, Wis.; distilled before use). 1.3 Grams (3.85 mmol) of Fmoc-N-hydroxysuccinimide was added and the solution was left at room temperature for 10 hours. The solution was evaporated to dryness in vacuo. The residue was dissolved in 100 ml ethyl acetate and washed with 50 ml of 5% $NaHCO_3$. The solution was filtered and the $NaHCO_3$ wash was repeated two more times. The precipitate from the three $NaHCO_3$ washes was then extracted with a mixture of three parts (v/v) ethyl acetate to one part saturated $KHSO_4$. The organic layer was isolated and concentrated in vacuo. After removal of most of the ethyl acetate by vacuum the product was precipitated with petroleum ether. The product was recrystallized twice using an ethyl acetate-petroleum ether mixture to yield 0.83 g (64%) with a melting point of 118–120° C. Thin layer chromatography was performed according to well-known procedures and displayed a spot with Rf=0.28. $[\alpha]_D^{21}=-6.29$ (c1.7, DMF).

Anal. calc. for $C_{29}H_{30}N_2O_6$: C, 69.31, H. 6.02. Found: C, 68.68, H, 6.14.

EXAMPLE 2

Synthesis of (S)-a-[[1,1-dimethylethoxy)carbonyl]-amino]-1-napthalenepropanoic acid (Boc-NA)

3(1'-Naphthyl)alanine (2.3 mmol; 0.5 g) was dissolved in a mixture of 4 ml dioxane, 4 ml water and 1.28 ml (9.22 mmol) of TEA. 0.76 Grams (3.46 mmol) of di-tert-butyl-dicarbonate was added and the mixture was stirred for 10 hours at room temperature, then evaporated to dryness in vacuo. The residue was redissolved in 20 ml of water and with 10 ml of hexane. The hexane extraction was repeated for a total of three extractions and the aqueous layer was removed and acidified by the addition of saturated $KHSO_4$ until precipitation occurred. The suspension was next extracted with ethyl acetate, the organic layer was isolated, dried with $MgSO_4$, filtered and concentrated in vacuo. The product was precipitated from petroleum ether in accordance with the teaching of Example 1 to yield 0.66 g (90%) of the desired product. Thin layer chromatography was performed and displayed a spot with Rf=0.54.

EXAMPLE 3

Synthesis of Peptides

The retrovirus protease inhibitory peptides of the present invention were synthesized using the classic Merrifield method of stepwise solid phase peptide synthesis. Detailed explanations of the various reactions (such as preparation of Boc Amino Acids, thin layer chromatography, ninhydrin tests, etc.) can be found in Stewart and Young, 1984, *Solid Phase Peptide Synthesis*, Second Edition (Pierce Chemical Company), the entire teaching of which is herein incorporated by reference.

Synthesis of each of the peptides were started with the coupling of the first amino acid to the p-methylbenzhydrylamine resin hydrochloride (United States Biochemical, Cleveland, Ohio). The addition of each Boc-amino acid was accomplished by adding 2.5 equivalents of the Boc-amino acid to the resin, except for the addition of Boc-Statine (Advanced Chem Tech, Louisville, Ky.) and Boc-ACHPA, when only 1.25 equivalents were used. Boc-ACHPA was produced in substantial accordance with the teaching of Hui et al. 1987, J. Med. Chem. 30:1287–1295 and Boger et al., 1985, J. Med. Chem. 28:1779, the teachings of which are herein incorporated by reference. The stepwise synthesis of H-Pro-paF-Pro-Phe-Val-Statine-Leu-Phe-paF—NH$_2$(P-1) was performed as described below.

A. Preparation of Resin and Incorporation of Boc-Amino Acids

Before adding the Boc-amino acid, 0.45 g of p-methylbenzhydrylamine HCl resin (containing 0.33 mmol of the free amino group) was washed three times with 10 ml (each wash) dichloromethane (DCM). Dichloromethane was used as a solvent for the Boc-amino acids and coupling agents, therefore 5 ml of DCM containing 2.5 equivalents of Boc-para-(Fmoc)aminophenylalanine (from Example 1) was added to the washed resin. N,N'-dicyclohexylcarbodiimide (DCC from Fluka, New York, N.Y.) was used as a condensing agent, therefore 1 ml of DCM containing 2.5 equivalents of DCC was added to the coupling reaction. This reaction was stirred at room temperature for one to two hours, then a small aliquot was removed.

After washing with DCM, an aliquot of the peptide/resin was placed in a test tube to prepare it for a ninhydrin test to monitor the coupling of the Boc-amino acid to the resin. A 70% phenol solution (in EtOH) was prepared and one drop of this solution was added to the peptide/resin in a test tube. One drop of a pyridine solution (containing 0.0002 M potassium cyanide) was added, then one drop of a ninhydrin solution (0.28 $\underline{M}$ in EtOH) was added. The test tube containing the test mixture was heated to 110° C. for two minutes. A blue or amber color indicates the presence of free amino groups while a light yellow color indicates the absence of free amino groups.

Alternatively, the ninhydirin test can be performed upon this small aliquot as follows. The aliquot is washed twice with a solution of 5% triethylamine in DCM, then three times with DCM, followed by drying in vacuo. Two to five mgs are weighed out and placed into a test tube. 0.1 ml KCN (treated with Amberlite MB-3 to remove ammonia), 0.04 ml ninhydrin and 0.05 ml phenol (also treated with MB-3) are added to the dried resin. This solution is heated to 100° C. for 10 minutes, then chilled in cold water. One ml of 60% ethanol is added, then the solution is mixed and filtered through a glass wool plug. The tube is rinsed twice with 0.2 ml of tetraethylammonium chloride (0.5 M) in DCM, then the combined filtrates and washes are brought up to 2.0 ml with 60% ethanol. The absorbance is read at 570 nm against a reagent blank. A light color indicates a high percentage of coupling. The ninhydrin test is adapted from Steward and Young, supra, and Kaiser et al., 1970, *Anal. Biochem.*, 34:595, the teachings of which are herein incorporated by reference.

B. Removal of the Boc Protecting Group

Following the coupling reaction, the resin was washed three times with 10 ml (each wash) dichloromethane. Next, 15 ml of TFA (50% trifluoroacetic acid in DCM) were added and the solution was stirred for one minute. The supernatant was removed from the resin, then another 15 ml of TFA were added and stirring continued for 30 minutes. Following the removal of the supernatant, the resin was again washed three times with 10 ml (each wash) DCM. A small aliquot of the resin was removed and the ninhydrin test was performed to monitor the reaction.

C. Neutralization

Before the next Boc-amino acid was coupled to the peptide/resin, the peptide resin was neutralized using N,N-diisopropylethylamine (DIEA, from Aldrich, Milwaukee, Wis.). Fifteen mls of a DIEA solution (5% DIEA in DCM) was added to the resin and stirred for one minute. The supernatant was removed and another 15 ml of the DIEA solution was added and the resin was stirred for five minutes. This supernatant was removed, the peptide resin was washed six times with DCM, and the next Boc-amino acid solution was added to the resin.

Steps A, B, and C were sequentially repeated using the appropriate Boc-protected amino acids (commercially available from Peninsula Laboratories, San Carlos, Calif.) to produce a completed peptide/resin having the sequence Boc-Pro-paF(Fmoc)-Pro-Phe-Val-Statine-Leu-Phe-paF (Fmoc)-resin. The only change in the procedure occurred with Boc-Statine (Advanced Chem Tech) was added. When adding Boc-Statine, 1.25 equivalents of the amino acid and 1.25 equivalents of the condensing reagent (DCC) were used. The coupling reaction for Boc-Statine was allowed to run for 10 hours, rather than the 1 hour reaction time normally used. Alternatively, larger excesses of Boc-Statine or longer coupling times can be used.

D. Removal of the Fmoc Group

A solution of 30% piperidine in dimethylformamide (DMF) was prepared, then 10 ml of this solution was added to the peptide/resin, which was stirred for two hours. The supernatant was removed and another 10 ml of the piperidine solution was added and stirring was continued for another two hours. The supernatant was again removed and the peptide resin was washed with 10 ml of ethanol. An aliquot was removed and the ninhydrin test showed a reddish-brown resin.

The peptide/resin was next treated with 10 ml of a 0.05 N NaOH/ethanol solution for 10 minutes with stirring. The supernatant was removed and the resin was washed three times with ethanol (10 ml each wash) followed by three washes with DCM (10 ml each wash). The remaining Boc group was then removed as in substantial accordance with the teaching of Example 3B.

E. Cleavage of Peptide from Resin

The peptide H-Pro-paF-Pro-Phe-Val-Statine-Leu-Phe-paF—NH$_2$(P-1) was released from the resin by stirring for 45 minutes at 0° C. in a solution of 10 parts (v/v) HF (Mateson, Secaucus, N.J.) containing 10% anisole to 1 part resin. After removal of most of the HF by vacuum the peptide was washed with anhydrous ether. The free peptide was extracted with 1 $\underline{M}$ acetic acid, 50% acetic acid and then water. The extracts were pooled and lyophilized.

The fully deprotected peptide gave the following amino acid composition upon hydrolysis: Pro, 2.06(2); Phe, 2.02 (2); Val, 0.99(1); Leu, 0.99(1); Statine, 0.99(1); paF, 2.02(2); which corresponds to the proper ratios for the P-1 peptide.

In addition to the P-1 peptide, the following peptides in Table II were also constructed in substantial accordance with the teachings set forth above. The active amino acid composition of the peptides is listed after each residue while the theoretical composition is listed in parenthesis.

TABLE II

P-1   H-Pro paF Pro Phe Val         Statine Leu Phe paF NH$_2$
Pro, 2.06 (2); Phe, 2.02 (2); Val, 0.99 (1); Leu, 0.99 (1);
paF, 2.02 (2); Statine 0.99 (1)
P-2   H-Pro His Pro Phe Val         ACHPA Leu Phe paF NH$_2$
Pro, 2.04 (2); His, 1.09 (1); Phe, 1.88 (2); Val, 0.95 (1);
Leu, 1.05 (1); paF, 0.88 (1); ACHPA, Present (1)
P-3   H-Pro paF Pro Phe Val         ACHPA Leu Phe paF NH$_2$
Pro, 2.00 (2); paF, Present (2); Phe, 2.02 (2); Val, 0.98 (1);
Leu, 1.00 (1); ACHPA, Present (1)
P-4   Ac paF Pro Phe Val            ACHPA Leu Phe paF NH$_2$
paF, Present (2); Pro, 1.06 (1); Phe, 1.96 (2); Val, 0.97 (1);
Leu, 1.00 (1); ACHPA, Present (1)
P-5   Ac Tyr Pro Phe Val            Statine Leu Phe NH$_2$
Tyr, 0.82 (1); Pro, 1.05 (1); Phe, 2.13 (2); Val, 0.98 (1);
Leu, 1.00 (1); Statine, 1.02 (1)
P-6   Ac His Pro Phe Val            Statine Leu His NH$_2$
His, 1.79 (2); Pro, 1.12 (1); Phe, 1.03 (1); Val, 1.00 (1);
Leu, 1.06 (1); Statine, 0.93 (1)
P-7   Ac NA Pro Phe Val             Statine Leu Phe NH$_2$
NA, 1.05 (1); Pro, 0.99 (1); Phe, 2.00 (2); Val, 1.00 (1);
Leu, 0.97 (1); Statine, 0.79 (1)

TABLE II-continued

| | | | | |
|---|---|---|---|---|
| P-8 | Ac Trp Pro Phe Val | Statine | Leu Phe NH$_2$ | |
| Trp, Present (1); Pro, 1.03 (1); Phe, 2.03 (2); Val, 0.99 (1); Leu, 0.94 (1); Statine, 1.01 (1) | | | | |
| P-9 | Ac YOM Pro Phe Val | Statine | Leu Phe NH$_2$ | |
| Tyr, 0.82 (1); Pro, 1.06 (1); Phe, 2.10 (2); Val, 1.01 (1); Leu, 0.98 (1); Statine, 1.02 (1) | | | | |
| P-10 | Ac Phe Pro Phe Val | Statine | Leu Phe NH$_2$ | |
| Phe, 3.16 (3); Pro, 0.96 (1); Val, 0.93 (1); Leu, 0.95 (1); Statine, 1.08 (1) | | | | |
| P-11 | H-Pro His Pro Phe His | Statine | Leu Phe NH$_2$ | |
| Pro, 2.10 (2); His, 2.02 (2); Phe, 2.01 (2); Leu, 0.97 (1); Statine, 0.79 (1) | | | | |
| P-12 | Ac paF Pro paF Val | Statine | Leu Phe paF NH$_2$ | |
| paF, 3.24 (3); Pro, 0.97 (1); Val, 0.93 (1); Leu, 0.97 (1); Phe, 1.10 (1); Statine 1.06 (1) | | | | |
| P-13 | Ac paF Pro YOM Val | Statine | Leu Phe paF NH$_2$ | |
| paF, 2.00 (2); Pro, 1.00 (1); Tyr, 0.69 (1); Val, 0.88 (1); Leu, 0.93 (1); Phe, 1.20 (1); Statine, 1.00 (1) | | | | |
| P-14 | Ac paF Pro Phe Val | Statine | Leu Phe paF NH$_2$ | |
| paF, 2.16 (2); Pro, 1.09 (1); Phe, 2.07 (2); Val, 0.95 (1); Leu, 0.98 (1); Statine, 1.08 (1) | | | | |
| P-15 | H-His Pro Phe Val | Statine | Leu Phe paF NH$_2$ | |
| His, 1.00 (1); Pro, 1.08 (1); Phe, 2.03 (2), Val, 0.94 (1); Leu, 0.95 (1); paF, 0.88 (1); Statine, 0.88 (1) | | | | |
| P-16 | Ac His Pro Phe Val | ACHPA | Leu Phe His NH$_2$ | |
| His, (2); Pro, (1); Phe, (2); Val, (1); Leu, (1); ACHPA, (1) | | | | |
| P-17 | Ac His Pro Phe Val | ACHPA | Leu Phe paF NH$_2$ | |
| His, 0.98 (1); Pro, 0.96 (1); Phe, 2.11 (2); Val, 0.92 (1); Leu, 1.03 (1); paF, Present (1); ACHPA, Present (1) | | | | |
| P-18 | Ac His Pro Phe His | ACHPA | Ile Phe NH$_2$ | |
| His, 2.07 (2); Pro, 0.86 (1); Phe, 2.10 (2); Ile, 0.74 (1); ACHPA, 1.07 (1) | | | | |
| P-19 | H-Pro His Pro Phe His | Statine | Ile His NH$_2$ | |
| Pro, 2.10 (2); His, 2.70 (3); Phe, 1.15 (1); Ile, 1.04 (1); Statine, 0.48 (1) | | | | |
| P-20 | Ac His Pro Phe Val | Statine | Leu Phe Leu NH$_2$ | |
| His, 1.00 (1); Pro, 0.97 (1); Phe, 2.10 (2); Val, 0.96 (1); Leu, 1.85 (2); Statine, 0.87 (1) | | | | |
| P-21 | Ac His Pro Phe Val | Statine | Leu Phe Phe NH$_3$ | |
| His, 1.00 (1); Pro, 0.98 (1); Phe, 3.09 (3); Val, 0.95 (1); Leu, 0.94 (1); Statine, 0.80 (1); | | | | |
| P-22 | Ac His Pro Phe Val | Statine | Leu Leu Phe NH$_2$ | |
| His, 0.95 (1); Pro, 0.96 (1); Phe, 2.25 (2); Val, 0.85 (1); Leu, 1.80 (2); Statine, 1.12 (1); | | | | |
| P-23 | H-Pro His Pro Phe His | Statine | Ile Phe NH$_2$ | |
| Pro, 2.02 (2); His, 2.02 (2); Phe, 2.07 (2); Ile, 0.96 (1); Statine, 1.06 (1) | | | | |
| P-24 | H-Pro His Pro Phe His | AHPPA | Ile Phe NH$_2$ | |
| Pro, 2.22 (2); His, 1.91 (2); Phe, 1.87 (2); Ile, 0.86 (1); AHPPA, Present (1) | | | | |
| P-25 | H-Pro His Pro Phe His | AVA | Ile Phe NH$_2$ | |
| Pro, 2.20 (2); His, 1.97 (2); Phe, 1.97 (2); Ile, 0.86 (1); AVA, 1.24 (1) | | | | |
| P-26 | Ac paF Pro Phe Val | Statine | Leu Phe NH$_2$ | |
| paF, (1); Pro, (1); Phe, (2); Val, (1); Leu, (1); Statine, (1) | | | | |
| P-27 | Ac NA Ser Phe Val | Statine | Leu Phe NH$_2$ | |
| NA, (1); Ser, (1); Phe, (2); Val, (1); Leu, (1); Statine, (1) | | | | |
| P-28 | H-Pro paF Pro Phe Val | R, S-Sta | Leu Phe paF NH$_2$ | |
| Pro, (2); paF, (2); Phe, (2); Val, (1); Leu, (1); R, S-Sta, (1) | | | | |
| P-29 | Ac Gly Tyr YOM Pro Phe Val | Statine | Leu Phe NH$_2$ | |
| Gly, (1); Tyr, (1); YOM, (1); Pro, (1); Phe, (2); Val, (1); Leu, (1); Statine, (1) | | | | |
| P-30 | Ac YOM Pro Phe Val | Statine | Leu Phe Tyr Leu NH$_2$ | |
| YOM, (1); Pro, (1); Phe, (2); Val, (1); Leu, (2); Tyr, (1); Leu, (1); Statine, (1) | | | | |
| P-31 | Ac Phe Val | Statine | Leu Phe NH$_2$ | |
| Phe, (2); Val, (1); Leu, (1); Statine, (1) | | | | |

EXAMPLE 4

Inhibition of HIV-1 Protease Produced in *E. coli*

A. Culture of *E. coli* K12 L507/pHP10D

Lyophils of *E. coli* K12 L507/pHP10D are obtained from the Northern Regional Research Laboratory, Peoria, Ill. 61604, under the accession number NRRL B-18560 (deposited Nov. 14, 1989). The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 12.5 μg/ml in tetracycline and then incubated at 32° C. overnight.

A small portion of the overnight culture was placed on LB-agar (LB medium with 15 g/l Bacto-agar) plates containing 12.5 μg/ml tetracycline in a manner so as to obtain a single colony isolate of *E. coli* K12 L507/pHP10D. The single colony obtained was inoculated into 10 ml of LB medium containing 12.5 μg/ml tetracycline and incubated overnight at 32° C. with vigorous shaking. The 10 ml overnight culture was inoculated into one liter of LB medium containing 12.5 μg/ml tetracycline and incubated at 32° C. with vigorous shaking until the culture reached mid-log phase. A restriction site and function map of plasmid pHP10D is presented in FIG. 1 of the accompanying drawings.

B. Culture of *E. coli* K12 L507/pHGAG

Lyophils of *E. coli* K12 L507/pHGAG are obtained from the NRRL under the accession number NRRL B-18561 (deposited Nov. 14, 1989). A purified colony of *E. coli* K12 L507/pHGAG was isolated, and used as an inoculum for a one liter culture which was grown to mid-log phase in substantial accordance with the teaching of Example 4A. A restriction site and function map of plasmid pHGAG is presented in FIG. 2 of the accompanying drawings.

C. Preparation of Protease and gag Fractions

A one liter culture of *E. coli* K12 L507/pHP10D was grown to mid-log phase at 32° C. in LB media containing 12.5 μg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 8 ml Lysis buffer. Lysis buffer was comprised of 50 mM Tris-HCl (pH 7.8), 5 mM EDTA, 1 mM DTT, 100 mM NaCl, 1 μg/ml E64 and 2 μg/ml aprotinin. Lysozyme was added to the culture to a concentration of 5 mg/ml, then the culture was stirred at 4° C. for 30 to 60 minutes. The cells were then sonicated for three 20 second bursts, with chilling between bursts, in a Branson® Cell Disrupter set on 60% power. About 80% of the HIV-1 protease was bound to the insoluable fraction of the lysed cells. This crude lysate was stored at −20° C. in 50% glycerol and lysis buffer.

In an analogous manner, a one liter culture of *E. coli* K12 507/pHGAG was grown to mid-log phase at 32° C. then shifted to 40° C. for about 4 to 5 hours. The culture was chilled on ice and centrifuged, then the pellet was resuspended in 8 ml lysis buffer containing 5 mg/ml lysozyme. The culture was incubated about 30 to 60 minutes at 4° C., then briefly sonicated in a Branson® Cell Disrupter at 60% power, for three 20 second bursts with chilling between each burst. The culture was then centrifuged at 15,000 g and the supernatant, which contains the unprocessed gag protein, was stored at −20° C. in 50% glycerol and lysis buffer.

E. Protease Inhibition Assay

About 10 to 20 μl of the crude protease lysate was mixed with about 2 μl of the gag supernatant. The mixture was then brought to a total volume of 100 μl by the addition of distilled water, MES buffer (2-[N-Morpholino] ethanesulfonic acid) (pH 5.5 to a total concentration of 50 mM), DTT (dithiolthreitol) (to a total concentration of 1 mM) and NaCl (to a total concentration of 25 mM). This reaction mixture was mixed gently then incubated from 3 hours to overnight at 37° C.

Next, about 25 μl of the reaction was mixed with loading buffer and subjected to polyacrylamide gel electrophoresis on a 12.5% Laemmli gel under reducing conditions. The proteins were transferred onto a nitrocellulose filter using standard "Western Blot" electrophoresis at 500 mAmps for 35 minutes at room temperature. The filter was air-dried, then non-specific immunoreaction was blocked by washing the filter for 30 minutes at 4° C. in a solution of 3% non-fat dry milk powder in phosphate buffered saline (PBS).

Monoclonal antibodies against p17 and/or p24 (available from DuPont, Wilmington, Del.) were added to about 40 ml of the 3% milk/PBS solution to a final concentration of 2 µg/ml. The nitrocellulose filter was added to the antisera solution and slowly rocked for 2 hours at 4° C. The filter then was removed and washed 5 times with PBS, then the maturation of the gag gene was determined by reaction with $I^{125}$-labeled protein A or by reaction with biotinylated anti-mouse IgG antibodies (Vecta Stain®).

To run the $I^{125}$-labeled protein A reaction, about 10 µCi of $I^{125}$-labeled protein A was added to 100 ml of the 3% milk/PBS solution. The filter was rocked in this solution for 2 hours at 4° C., washed three times with PBS, then two times with PBS and 0.1% Tween 20. The filter was then air-dried and exposed to x-ray film for autoradiography.

The Vecta Stain® (Vector Laboratories, Burlingome, Calif.) procedure was performed according to the manufacturer's recommendations. Four drops of the biotinylated IgG was added to 40 mls of the 3% Milk/PBS solution, then the filter was rocked in this solution for 60 minutes at 4° C. The filter was washed five times with PBS, then rocked for 30 to 60 minutes at 4° C. in Reagent ABC. Reagent ABC was prepared by adding 4 drops of Reagent A (Avidin DH) and 4 drops of Reagent B (biotinylated peroxidase) to 20 ml of 3% Milk/PBS. The filter was then washed five times with PBS, then the filter was developed by washing it for 5 to 10 minutes in 10 ml of PBS containing 0.02% $H_2O_2$ and 10 ml of 4-chloro-1 naphthol. When the color was fully developed, the filter was washed with distilled water and air-dried.

Following the procedure, it is simple to determine the activity of the HIV-1 protease encoded on plasmid pHP10D and produced in *E. coli* cells. When the protease is fully active, the gag protein, encoded by plasmid pHGAG and produced in *E. coli*, is cleaved from the precursor gag form into mature p24 and p17 proteins, which are readily measured by their presence relative to the precursor protein. The addition of an HIV-1 protease inhibitor to the reaction prevents the maturation of the gag protein, an event which is easily determined using gel electrophoresis and Western Blotting.

The HIV-1 protease inhibition activity of each of the peptides produced in Example 3 was tested using this method. The peptides were diluted, then aliquots of the peptides were added to the crude lysate of the protease and the protease and peptide were "preincubated" at room temperature for 60 minutes. The gag lysate, MES buffer, DTT and NaCl were then added to the proper final concentrations and the reaction mixture was incubated overnight at 37° C. The reaction mixtures were then electrophoresed, "Western Blotted" and developed to determine the inhibitory activity of the peptides. The peptides were tested at final reaction concentrations of $10^{-4}$ M, $10^{-5}$ M and $10^{-6}$ M. Those reactions which demonstrated no maturation of the gag precursor into mature p24 and p17 proteins were graded "4+." Those reactions which showed little maturation were graded "3+," while a grade of "2+" indicated a bit more maturation. Reactions graded "1+" indicate a reasonable amount of gag maturation, while reactions graded "–" were considered to be equivalent to the control reactions where no protease inhibitor was added and therefore the gag protein was fully cleaved into p24 and p17. The results of the screening are presented in Table III.

TABLE III

| | | | | | (Concentration Added) Relative Inhibition | | |
|---|---|---|---|---|---|---|---|
| | Inhibition of HIV-1 Protease Activity | | | | ($10^{-4}$ M) | ($10^{-5}$ M) | ($10^{-6}$ M) |
| P-1 | H—Pro paF Pro Phe Val | Statine | Leu Phe paF NH$_2$ | | 4+ | 4+ | 3.5+ |
| P-2 | H—Pro His Pro Phe Val | ACHPA | Leu Phe paF NH$_2$ | | 4+ | 3+ | 1+ |
| P-3 | H—Pro paF Pro Phe Val | ACHPA | Leu Phe paF NH$_2$ | | 2+ | 1+ | – |
| P-4 | Ac paF Pro Phe Val | ACHPA | Leu Phe paF NH$_2$ | | 3+ | 2+ | – |
| P-5 | Ac Tyr Pro Phe Val | Statine | Leu Phe NH$_2$ | | 3+ | 2+ | – |
| P-6 | Ac His Pro Phe Val | Statine | Leu His NH$_2$ | | – | – | – |
| P-7 | Ac NA Pro Phe Val | Statine | Leu Phe NH$_2$ | | 4+ | 3+ | 1.5+ |
| P-8 | Ac Trp Pro Phe Val | Statine | Leu Phe NH$_2$ | | 3+ | 2+ | 1+ |
| P-9 | Ac YOM Pro Phe Val | Statine | Leu Phe NH$_2$ | | 4+ | 4+ | 3+ |
| P-10 | Ac Phe Pro Phe Val | Statine | Leu Phe NH$_2$ | | 3+ | 2+ | 1+ |
| P-11 | H—Pro His Pro Phe His | Statine | Leu Phe NH$_2$ | | – | – | – |
| P-12 | Ac paF Pro paF Val | Statine | Leu Phe paF NH$_2$ | | 3+ | 2+ | 1+ |
| P-13 | Ac paF Pro YOM Val | Statine | Leu Phe paF NH$_2$ | | 4+ | 2+ | 1+ |
| P-14 | Ac paF Pro Phe Val | Statine | Leu Phe paF NH$_2$ | | 3+ | 1+ | – |
| P-15 | H—His Pro Phe Val | Statine | Leu Phe paF NH$_2$ | | 4+ | 4+ | 2.5+ |
| P-16 | Ac His Pro Phe Val | ACHPA | Leu Phe His NH$_2$ | | 2+ | 1+ | – |
| P-17 | Ac His Pro Phe Val | ACHPA | Leu Phe paF NH$_2$ | | 2+ | 1+ | – |
| P-18 | Ac His Pro Phe His | ACHPA | Ile Phe NH$_2$ | | – | – | – |
| P-19 | H—Pro His Pro Phe His | Statine | Ile His NH$_2$ | | – | – | – |
| P-20 | Ac His Pro Phe Val | Statine | Leu Phe Leu NH$_2$ | | – | – | – |
| P-21 | Ac His Pro Phe Val | Statine | Leu Phe Phe NH$_3$ | | 4+ | 2+ | 1+ |
| P-22 | Ac His Pro Phe Val | Statine | Leu Leu Phe NH$_2$ | | 2+ | 1+ | – |
| P-23 | H—Pro His Pro Phe His | Statine | Ile Phe NH$_2$ | | – | – | – |
| P-24 | H—Pro His Pro Phe His | AHPPA | Ile Phe NH$_2$ | | 2+ | 1+ | – |
| P-25 | H—Pro His Pro Phe His | AVA | Ile Phe NH$_2$ | | – | – | – |
| P-26 | Ac paF Pro Phe Val | Statine | Leu Phe NH$_2$ | | 4+ | 4+ | 4+ |
| P-27 | Ac NA Ser Phe Val | Statine | Leu Phe NH$_2$ | | 4+ | 4+ | 3+ |
| P-28 | H—Pro paF Pro Phe Val | R,S—Sta | Leu Phe paF NH$_2$ | | ND | ND | ND |

TABLE III-continued

| Inhibition of HIV-1 Protease Activity | | | (Concentration Added) Relative Inhibition | | |
|---|---|---|---|---|---|
| | | | ($10^{-4}$ M) | ($10^{-5}$ M) | ($10^{-6}$ M) |
| P-29 Ac Gly Tyr YOM Pro Phe Val | Statine | Leu Phe $NH_2$ | 4+ | 4+ | 3.5+ |
| P-30 Ac YOM Pro Phe Val | Statine | Leu Phe Tyr Leu $NH_2$ | 4+ | 4+ | 3.5+ |
| P-31 Ac Phe Val | Statine | Leu Phe $NH_2$ | 4+ | 4+ | 3.5+ |

EXAMPLE 5

Inhibition of HIV-1 in Cell Culture

Quantitative evaluation of the viral inhibition were performed on the T-cell lymphoblastoid cell lines MT-2 (Harada et al., 1985, Science 229:563–566) and CEM (Nara and Fischinger, 1988, Nature 332:469–470). The cells were infected with the HTLV-IIIB strain of HIV-1 from the supernatant fluid of infected human T-lymphocyte cell line H9 (Popovic, M. et al., 1984, Science 224:497–500). Each of these three cell lines are publicly available from the National Institutes of Health (NIH) AIDS Research and Reference Reagent Program. The H9/HTLC-IIIB cell line is available under catalogue number 231, while CEM cell line is available under catalogue number 117 and the MT-2 cell line is available under the catalogue number 237. MT-2 and CEM cells were grown in RPMI 1640 medium supplemented with 10% (v/v) fetal calf serum, 100 U/ml penicillin, 100 μg/ml streptomycin and 25 mM HEPEs buffer. H9 cells were grown in the same medium except 20% fetal calf serum was used. The peptides were diluted in the medium used for MT-2 and CEM cells. Cell cultures were maintained in disposable tissue culture labware at 37° C. in a humidified atmosphere of 5% $CO_2$ in air.

The inhibitors were dissolved in DMSO at 40 mg/ml or sterile water at 2 mg/ml, then dilutions were made in medium. The dilutions were added to micro-titer plates in 100 μl/well aliquots so that the high drug concentration for each screen was 100 μg/ml after the addition of cells to the well.

Susceptible MT-2 and CEM cells were grown and the cell population determined by a trypan blue viable cell count. The desired total number of cells were placed in a sterile, disposable 50 ml conical centrifuge tube and virus was added to give an MOI (Multiplicity of Infection) of 0.03 $TCID_{50}$/cell (Tissue Culture Infectious Dose) on MT-2 cells and approximately 0.12 $TCID_{50}$/cell on CEM cells. Fresh medium was added to adjust the cell density to $1 \times 10_5$ cells/ml, then the virus-cell suspension was incubated at 37° C. for 1 to 2 hours until plating. Uninfected controls cell were prepared in the same manner but without the addition of virus. Infected and uninfected cells were added to plates in 100 μl/well aliquots to give a starting cell number of $1 \times 10^4$ cells/well. The plates were incubated for seven days in a humidified atmosphere of 5% $CO_2$ in air.

Figure 3:
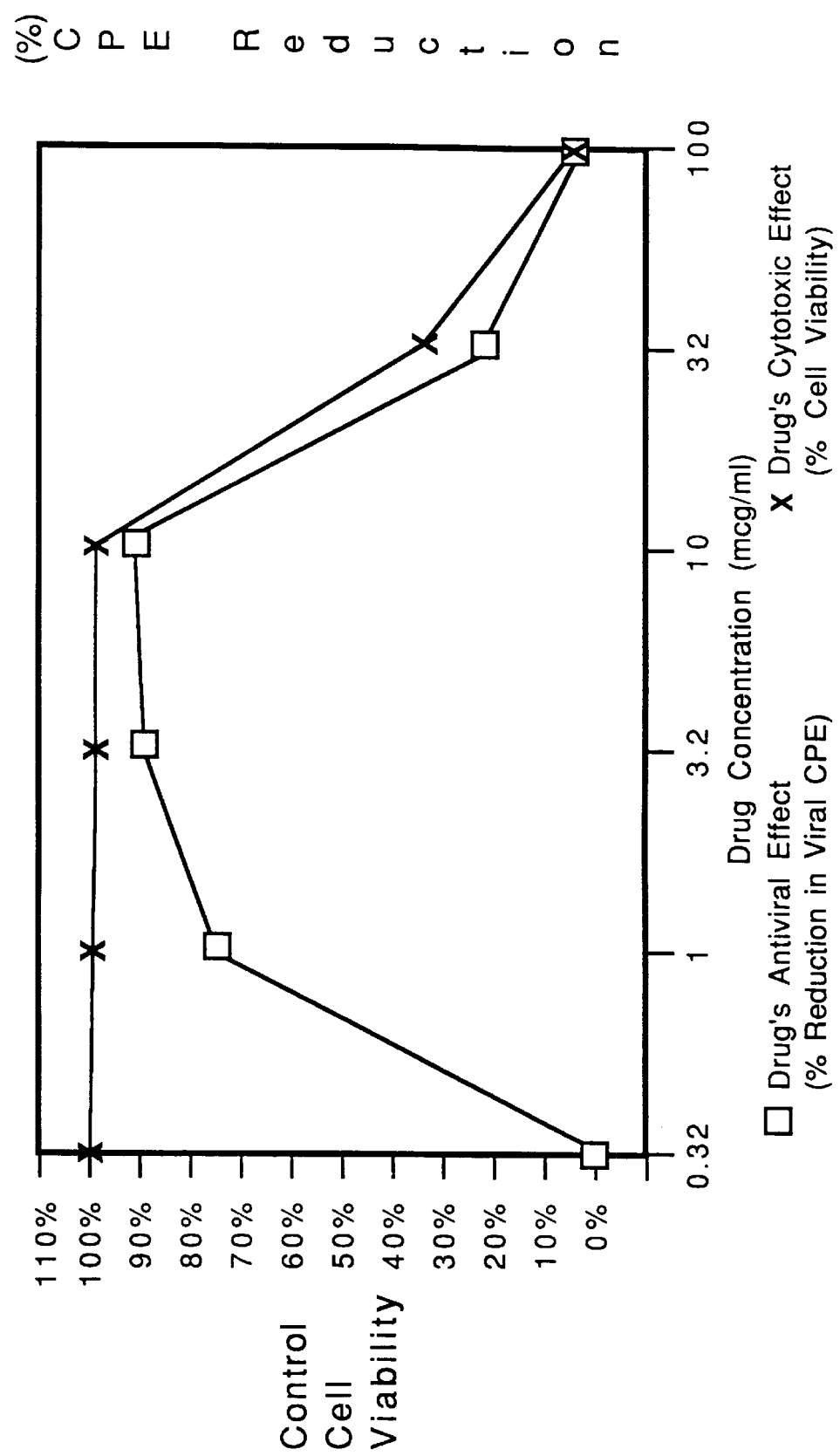
FIG. 3—a chart displaying the cytopathic effect and antiviral effect of peptide P-9. In the figure, a block represents the peptide's antiviral effect at a given concentration while an X represents the peptide's cytotoxic effect at a given concentration.

Reagents for colorimetric evaluation of cell viability were prepared by mixing the tetrazolium reagent, XTT, and phenazine methosulfate (PMS) to final concentrations of 200 μg/ml and 0.02 mM, respectively. Fifty microliters of the XTT-PMS solution was added to each well of the microtiter plates, then the plates were incubated in the $CO_2$ incubator for another four hours. The lids were removed from the plates and replaced with adhesive plate sealers. The plates were read with the sealers in place in a Vmax Plate Reader® at 450 nm and 650 nm. The cytopathic effect (CPE) and percentage of cell viability were then calculated. Results are presented in Table IV and in FIGS. 3 and 4.

TABLE IV

| Drug ID | Cell Line | $ID_{50}$[a] (μg/ml) | $MTC_{50}$[b] (μg/ml) | TI[c] |
|---|---|---|---|---|
| P-9 | CEM | <0.32 | 43.8 | >137 |
| P-9 | CEM | 0.54 | 55 | 101 |
| P-7 | CEM | 0.37 | 21 | 57 |
| P-15 | CEM | 78.9 | >100 | >1.3 |
| P-1 | CEM | — | >100 | — |
| P-1 | CEM | — | >100 | — |
| DDC[d] | CEM | >0.032 | 9.9 | >308 |
| DDC | CEM | >0.32 | 2.9 | >90 |
| P-9 | MT-2 | 0.58 | 63.6 | 109 |
| P-9 | MT-2 | 0.69 | 66.5 | 96 |
| P-7 | MT-2 | 0.64 | 24.4 | 38 |
| P-15 | MT-2 | — | >100 | — |
| P-15 | MT-2 | — | >100 | — |
| P-1 | MT-2 | — | >100 | — |
| P-1 | MT-2 | — | >100 | — |
| DDC | MT-2 | 0.11 | >10 | >93 |
| DDC | MT-2 | 0.10 | >10 | 101 |

[a]$ID_{50}$ = The minimum drug Concentration (μg/ml) that inhibited CPE by 50%, calculated by using a regression analysis program for semilog curve fitting.
[b]$MTC_{50}$ = The minimum cytotoxic drug concentration (μg/ml) that reduces cell viability to 50%.
[c]TI = Therapeutic index calculated by dividing the $MTC_{50}$ by the $ID_{50}$.
[d]DDC = 2', 3'-Dideoxycytidine (Pharmacia, Piscataway, New Jersey or Sigma, St. Louis, Missouri)

The activity and cytotoxicity of several other peptides were also assayed in CEM cells using the same procedure as described above. These assays also included toxicity and activity levels of both 25% and 50%. The results of these studies are presented in Table V.

TABLE V

| Drug ID | IC25 (μg/ml) | IC25 (μg/ml) | IC50 (μg/ml) | TC50 (μg/ml) |
|---|---|---|---|---|
| P-9 | 1.78 | >100 | 12.0 | >100 |
| P-7 | 0.20 | >10 | 1.55 | >10 |
| P-10 | 0.51 | 49 | 1.15 | 55 |
| P-8 | 0.82 | 49 | 1.84 | 66 |
| P-5 | 1.33 | >100 | 6.14 | >100 |
| DDC | 0.0032 | 0.04 | ND | 0.8 |
| AZT | <0.0032 | >1.0 | <0.0032[a] | >1.0 |

IC25, I50 = concentration that reduced CPE by 25% and 50%, respectively.
TC25, TC50 = concentration that reduced cell viability by 25% and 50%, respectively.
ND = Not Done; 50% inhibition not reached.
[a] =Maximum inhibition reached was 60%, then inhibition decreased as drug concentration increased.

EXAMPLE 6

Inhibition of Murine Leukemia Virus in Cell Culture

About 3 to $5 \times 10^3$ SC-1 cells (available from the American Type Culture Collection, Rockville, Md. under the accession number ATCC CRL-1404) per well of a 96-well microtiter plate were seeded in minimal essential medium supplemented with 5% fetal bovine serum, penicillin (150 U/ml), Streptomycin (150 μg/ml) and polybrene (2 μg/ml), then infected with Mo-MuLV (Multiplicity of Infection=10 PFU/cell) the next day. The virus was allowed to adsorb to the cells for 1 hour, then medium containing serial dilutions of P-7, P-9 or medium alone was added to the cells. Pepstatin A (Isovaline-Val-Val-Statine-Ala-Statine) and AZT (3'-Azido-3'-deoxythymidine) were also added as controls. After incubation for 5 days (when cells were confluent) the SC-1 cells were UV irradiated for 10 seconds and 5 to $8 \times 10^4$ XC cells (ATCC CCL-165) per well were added. Generally, about two additional days of incubation were required to obtain full virus-induced cytopathic effect. The Moloney Murine Leukemia Virus Assay results are summarized in Table VI.

TABLE VI

| Compound | Dilution (μg/ml) | | | | | | | |
|---|---|---|---|---|---|---|---|---|
| | 200 | 100 | 50 | 25 | 12.5 | 6.25 | 3.12 | 1.56 |
| P-9 | ND | ND | 3+ | 2+ | – | – | – | – |
| P-7 | ND | ND | 3+ | 2+ | 1+ | – | – | – |
| Pepstatin A | ND | ND | – | – | – | – | – | – |
| | .2 | .1 | .05 | .025 | .012 | .006 | .003 | .015 | .0008 | .0004 |
| AZT | 4+ | 4+ | 4+ | 4+ | 4+ | 3+ | 2+ | 1+ | – | – |

CPE inhibition score as 4+(>90%) 3+(>60%) 2+(>40%) 1+(>20%) –(Negative)

The assay described above was also preferred to determine the virus yield. In this experiment, the supernatents were removed from the SC-1 cells four days after infection and tested for MLV titers, using the XC-plaque assay as previously described. The results are summarized in Table VII.

TABLE VII

MLV XC Plague Reduction Assay-Virus Yield

| Sample | Concentration | Yield (PFU/ML) | % Inhibition |
|---|---|---|---|
| Control | (no drug) | $1.9 \times 10^5$ | — |
| P-9 | 50 μg/ml | $3.0 \times 10^3$ | 98 |
| | 25 μg/ml | $1.2 \times 10^4$ | 94 |
| | 12.5 μg/ml | $5.5 \times 10^4$ | 71 |
| | 6.25 μg/ml | $9.0 \times 10^4$ | 54 |
| P7 | 50 μg/ml | $8.0 \times 10^3$ | 96 |
| | 25 μg/ml | $2.1 \times 10^4$ | 89 |
| | 12.5 μg/ml | $3.2 \times 10^4$ | 83 |
| | 6.25 μg/ml | $3.9 \times 10^4$ | 79 |
| Pepstatin | 50 μg/ml | $1.2 \times 10^4$ | 94 |
| | 25 μg/ml | $9.0 \times 10^4$ | 52 |
| AZT | 25 ag/ml | <10 | >99 |
| | 12.5 ng/ml | <10 | >99 |
| | 6.25 ng/ml | 80 | >99 |
| | 3.125 ng/ml | $2.9 \times 10^4$ | 98 |

EXAMPLE 7

In vivo Inhibition of Friend Virus Complex

Formulations of peptides P-9 and P-7 were prepared for injection into DBA/2 mice. The formulations were prepared by dissolving the purified peptides in Emulphor™ EL620 which was purchased from the GAF Chemical Corporation, 1361 Alps Row, Wayne, N.J., 07470. The drugs were injected intraperitoneally one hour before the mice were infected with a complex of Friend's Spleen-Forcus Virus (Fr. SFFV) and Friend's Murine Leukemia Virus (F. MLV). These viruses ordinarily cause polycythermia (elevated levels of red blood cells) and splenomegaly (enlargement of spleen) within two to three week post-infection. The mice were injected twice daily with the inhibitor formulation for twenty days after the infection. Results from the in vivo experiments are shown in Table VIII.

TABLE VIII

| Number | Treatment* | Spleen (gm) | Inhibition % | Virus Titer (PFU/ml)[a] | Inhibiton % |
|---|---|---|---|---|---|
| 1 | Uninf./Emulphor | 0.1 | — | 100 | — |
| 2 | Inf./Emulphor | 1.60 | 0 | 490,000 | 0 |
| 3 | Inf./Emulphor | 0.62 | 0 | 290,000 | 0 |
| 4 | Inf./100 pg P-9 | 1.29 | 0 | 280,000 | 28 |

TABLE VIII-continued

| Number | Treatment* | Spleen (gm) | Inhibition % | Virus Titer (PFU/ml)[a] | Inhibiton % |
|---|---|---|---|---|---|
| 5 | Inf./100 pg P-9 | 1.39 | 0 | 330,000 | 15 |
| 6 | Inf./100 pg P-9 | 0.23 | 80 | 200,000 | 49 |
| 7 | Inf./100 pg P-9 | 0.15 | 86 | 20,000 | 95 |
| 8 | Inf./100 pg P-7 | 1.11 | 0 | 320,000 | 18 |
| 9 | Inf./100 pg P-7 | 0.43 | 61 | 330,000 | 15 |
| 10 | Inf./100 pg P-7 | 0.49 | 56 | 150,000 | 62 |
| 11 | Inf./100 pg P-7 | 0.25 | 79 | 20,000 | 95 |
| 12 | Inf./100 pg AZT | 0.17 | 85 | 500 | >99 |
| 13 | Inf./100 pg AZT | 0.21 | 81 | 20,000 | 95 |

*Drugs were dissolved in Emulphor ™, injected IP one hour before infection, then twice daily for 20 days.
[a]Titers of Fr.MLV in the spleens (supernatents of 10% homogenates) were determined by XC plaque assay.

We claim:
1. A method for the inhibition of retroviral protease which comprises adding to a biological solution containing said retroviral protease an inhibitory amount of a compound of formula:

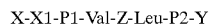

X-X1-P1-Val-Z-Leu-P2-Y wherein:
Z is Statine or ACHPA;
and when Z is Statine,
X is H-Pro-paF, H-Pro-His, Ac-Tyr, Ac-NA, Ac-Trp, Ac-YOM, Ac-Phe, Ac-paF, H-His Ac-His, or Ac-Gly-Tyr-YOM,
X1 is Pro, Ser, or Ac,
P1 is Phe, paF or YOM,
P2 is Phe or Leu, and
Y is $NH_2$, paF—$NH_2$, His—$NH_2$, Phe—$NH_2$ or Tyr-Lue—$NH_2$,
provided that when X1 is Ac then there is no X residue; and when Z is ACHPA, X is H-Pro-His, H-Pro-paF, Ac-PaF or Ac-His, P1 is Phe, P2 is Phe, and Y is paF—NH$_2$ and His—NH$_2$.

2. The method of claim 1 wherein the compound has the formula:

X-Pro-Phe-Val-ACHPA-Leu-Phe-Y wherein:

X is H-Pro-His, H-Pro-paF, Ac-paF or Ac-His, and

Y is paF—NH$_2$ and His—NH$_2$.

3. The method of claim 2 wherein the compound has the formula:

H-Pro-His-Pro-Phe-Val-ACHPA-Leu-Phe-paF—NH$_2$.

4. The method of claim 2 wherein the compound has the formula:

H-Pro-paF-Pro-Phe-Val-ACHPA-Leu-Phe-paF—NH$_2$.

5. The method of claim 2 wherein the compound has the formula:

Ac-paF-Pro-Phe-Val-ACHPA-Leu-Phe-paF—NH$_2$.

6. The method of claim 2 wherein the compound has the formula:

Ac-His-Pro-Phe-Val-ACHPA-Leu-Phe-paF—NH$_2$.

7. The method of claim 1 wherein the compound has the formula:

Ac-Na-Ser-Phe-Val-Statine-Leu-Phe—NH$_2$.

8. The method of claim 1 wherein the compound has the formula:

X-Pro-P1-Val-Statine-Leu-P2-Y wherein:

X is H-Pro-paF, H-Pro-His, Ac-Tyr, Ac-NA, Ac-Trp, Ac-YOM, Ac-Phe, Ac-paF, H-His, Ac-His or Ac-Gly-Tyr-YOM,

P1 is Phe, paF or YOM,

P2 is Phe or Leu and

Y is NH$_2$, paF—NH$_2$, His—NH$_2$, Phe—NH$_2$ or Tyr-Lue—NH$_2$.

9. The method of claim 8 wherein the compound has the formula:

X-Pro-Phe-Val-Statine-Leu-P2-Y wherein:

X is H-Pro-paF, H-Pro-His, Ac-Tyr, Ac-NA, Ac-Trp, Ac-YOM, Ac-Phe, Ac-paF, H-His, Ac-His or Ac-Gly-Tyr-YOM,

P2 is Phe or Leu and

Y is NH$_2$, paF—NH$_2$, His—NH$_2$, Phe—NH$_2$ or Tyr-Lue—NH$_2$.

10. The method of claim 9 wherein the compound has the formula:

X-Pro-Phe-Val-Statine-Leu-Phe—NH$_2$, wherein:

X is Ac-Tyr, Ac-NA, Ac-Trp, Ac-YOM, Ac-Phe or Ac-Gly-Tyr-YOM.

11. The method of claim 10 wherein the compound has the formula:

Ac-Tyr-Pro-Phe-Val-Statine-Leu-Phe—NH$_2$.

12. The method of claim 10 wherein the compound has the formula:

Ac-NA-Pro-Phe-Val-Statine-Leu-Phe—NH$_2$.

13. The method of claim 10 wherein the compound has the formula:

Ac-Trp-Pro-Phe-Val-Statine-Leu-Phe—NH$_2$.

14. The method of claim 10 wherein the compound has the formula:

Ac-YOM-Pro-Phe-Val-Statine-Leu-Phe—NH$_2$.

15. The method of claim 10 wherein the compound has the formula:

Ac-Phe-Pro-Phe-Val-Statine-Leu-Phe—NH$_2$.

16. The method of claim 10 wherein the compound has the formula:

Ac-Gly-Tyr-YOM-Pro-Phe-Val-Statine-Leu-Phe—NH$_2$.

17. The method of claim 8 wherein the compound has the formula:

H-Pro-paF-Pro-Phe-Val-Statine-Leu-Phe-paF—NH$_2$.

18. The method of claim 8 wherein the compound has the formula:

Ac-paF-Pro-paF-Val-Statine-Leu-Phe-paF—NH$_2$.

19. The method of claim 8 wherein the compound has the formula:

Ac-paF-Pro-YOM-Val-Statine-Leu-Phe-paF—NH$_2$.

20. The method of claim 8 wherein the compound has the formula:

Ac-paF-Pro-Phe-Val-Statine-Leu-Phe-paF—NH$_2$.

21. The method of claim 8 wherein the compound has the formula:

H-His-Pro-Phe-Val-Statine-Leu-Phe-paF—NH$_2$.

22. The method of claim 8 wherein the compound has the formula:

Ac-His-Pro-Phe-Val-Statine-Leu-Phe-Phe—NH$_2$.

23. The method of claim 8 wherein the compound has the formula:

Ac-His-Pro-Phe-Val-Statine-Leu-Leu-Phe—NH$_2$.

24. The method of claim 8 wherein the compound has the formula:

Ac-YOM-Pro-Phe-Val-Statine-Leu-Phe-Tyr-Lue—NH$_2$.

25. An antiviral method which comprises administering to an animal or cell culture which has been infected with a retrovirus an antiviral amount of a compound of formula:

X-X1-Phe-Val-Statine-Leu-P2-Y wherein:

X is H-Pro-paF, H-Pro-His, Ac-Tyr, Ac-NA, Ac-Trp, Ac-YOM, Ac-Phe, Ac-paF, H-His, Ac-His or Ac-Gly-Tyr-YOM,

X1 is Pro, Ser or Ac,

P2 is Phe or Leu and

Y is $NH_2$, paF—$NH_2$, H—$NH_2$, Phe—$NH_2$ or Tyr-Lue—$NH_2$, provided that when X1 is Ac then there is no X residue.

26. The method of claim 25 wherein the compound has the formula:

X-Pro-Phe-Val-Statine-Leu-Phe—$NH_2$, wherein:

X is Ac-Tyr, Ac-NA, Ac-Trp, Ac-YOM or Ac-Phe.

27. The method of claim 25 wherein the compound has the formula:

Ac-Tyr-Pro-Phe-Val-Statine-Leu-Phe—$NH_2$.

28. The method of claim 25 wherein the compound has the formula:

Ac-NA-Pro-Phe-Val-Statine-Leu-Phe—$NH_2$.

29. The method of claim 25 wherein the compound has the formula:

Ac-Trp-Pro-Phe-Val-Statine-Leu-Phe—$NH_2$.

30. The method of claim 25 wherein the compound has the formula:

Ac-YOM-Pro-Phe-Val-Statine-Leu-Phe—$NH_2$.

31. The method of claim 25 wherein the compound has the formula:

Ac-Phe-Pro-Phe-Val-Statine-Leu-Phe—$NH_2$.

32. The method of claim 25 wherein the compound has the formula:

Ac-Gly-Tyr-YOM-Pro-Phe-Val-Statine-Leu-Phe—$NH_2$.

33. The method of claim 25 wherein the compound has the formula:

Ac-YOM-Pro-Phe-Val-Statine-Leu-Phe-Tyr-Lue—$NH_2$.

34. The antiviral method of claim 25 wherein the animal or cell culture has the HIV-1 virus.

35. The antiviral method of claim 26 wherein the animal or cell culture has the HIV-1 virus.

36. The antiviral method of claim 27 wherein the animal or cell culture has the HIV-1 virus.

37. The antiviral method of claim 28 wherein the animal or cell culture has the HIV-1 virus.

38. The antiviral method of claim 29 wherein the animal or cell culture has the HIV-1 virus.

39. The antiviral method of claim 30 wherein the animal or cell culture has the HIV-1 virus.

40. The antiviral method of claim 31 wherein the animal or cell culture has the HIV-1 virus.

41. The antiviral method of claim 25 wherein the animal or cell culture has the HIV-2 virus.

42. The antiviral method of claim 26 wherein the animal or cell culture has the HIV-2 virus.

43. The antiviral method of claim 27 wherein the animal or cell culture has the HIV-2 virus.

44. The antiviral method of claim 28 wherein the animal or cell culture has the HIV-2 virus.

45. The antiviral method of claim 29 wherein the animal or cell culture has the HIV-2 virus.

46. The antiviral method of claim 30 wherein the animal or cell culture has the HIV-2 virus.

47. The antiviral method of claim 31 wherein the animal or cell culture has the HIV-2 virus.

48. A pharmaceutical formulation wherein the active ingredient is of the formula:

Ac-Gly-Tyr-YOM-Pro-Phe-Val-Statine-Leu-Phe—$NH_2$ or a pharmaceutically acceptable salt thereof.

* * * * *

UNITED STATES PATENT AND TRADEMARK OFFICE
CERTIFICATE OF CORRECTION

PATENT NO. : 6,001,810
DATED : December 14, 1999
INVENTOR(S) : Kwan Yuk Hui, Mei-Huei T. Lai It is certified that error appears in the above-identified patent and that said Letters Patent is hereby corrected as shown below:

Column 20, line 65 reads "Lue–NH$_2$,..." should read -- Leu–NH$_2$, ... --

Column 21, line 58 reads "Lue–NH$_2$...." should read -- Leu–NH$_2$.... --

Column 22, line 57 reads "...Lue–NH$_2$...." should read -- ...Leu–NH$_2$.... --

Column 23, line 3 reads "...or Tyr-Lue–..." should read -- ...or Tyr-Leu–...--

Column 24, line 3 reads "...Tyr-Lue–NH$_2$...." should read -- ...Tyr-Leu–NH$_2$....--

Signed and Sealed this

Twenty-first Day of November, 2000

Attest:

Q. TODD DICKINSON

Attesting Officer

Director of Patents and Trademarks